United States Patent [19]

Bennett

[11] Plant 4,911

[45] Nov. 2, 1982

[54] MINIATURE ROSE PLANT

[76] Inventor: Cecilia L. D. Bennett, 489 Minot Ave., Chula Vista, Calif. 92010

[21] Appl. No.: 213,744

[22] Filed: Dec. 5, 1980

[51] Int. Cl.[3] ..... A01H 5/00

[52] U.S. Cl. ..... Plt./7

[58] Field of Search ..... Plt./7

*Primary Examiner*—Robert E. Bagwill

[57] ABSTRACT

The subject of the present disclosure is a new and distinct variety of miniature rose plant characterized by the deep shell pink, edged with a deep orange-red on the outer petals, and the excellence of form for the petite size of the bloom.

1 Drawing Figure

1

The present invention relates to a new and distinct variety of hardy, dwarf, bush plant of the miniature class; the variety being primarily characterized a pink blend, similar in coloring to Tiki, a floribunda variety introduced in 1964 by Sam McGredy.

The variety is further characterized by:

An abundance of blooms borne singly on erect stems.

The bloom has a slight tea fragrance.

The plant is low growing, compact and well foliaged. The foliage is small, deep green, very serated and edged in bronze red. The bloom is similar in coloring to Tiki, a deep shell pink with outer petals edged in a deep orange-red when grown in the Chula Vista area. Tiki was introduced in 1964 by Sam McGredy.

The plant ranges in size from 8–12 inches, will get slightly larger when grown in the ground.

The present variety of miniature rose was originated by me at Tiny Petal's Nursery located at Chula Vista, Calif., under careful observation, and is a cross of "Over the Rainbow" a miniature as the pollen parent and "Little Darling" (U.S. Plant Pat. No. 1,581) the seed parent.

Subsequent to discovery of the variety I successfully reproduced it at Tiny Petal's Nursery located at aforesaid by cuttings and budding, with reproductions coming true in all respects.

The color photographs illustrate the variety.

Referring now specifically to the new and distinct variety of miniature rose plant, the following is a detailed description thereof in outline; all major color plate identification being by reference to the R.H.S. Horticultural Colour Chart.

Type: Hardy; dwarf; bushy; rounded; seedling; greenhouse; outdoors; cut flowers; garden decoration; potted plant.

Class: Miniature. Variety name: Luvvie.

Flowers borne: Usually one to a stem on short sturdy stems.

Quantity of bloom: Abundant both inside the greenhouse and outdoors.

Bud:

*Peduncle.*—Short. ¾" to ⅝". Sturdy; erect; reddish;

*Hairs.*—Very minute.

*Before calyx breaks.*—Size — small. Form short; pointed with a few foliaceous appendages and smooth on surface of the bud; with foliaceous parts extending beyond the tip of the bud to at least one-half or more of its length. Color — medium green tinted with red.

2

*As calyx breaks.*—Color — deep shell-pink with deep overtones of orange-red fading to a lighter shell-pink on the underside as the bloom opens.

*Opening.*—Opens well in all weather.

Bloom:

*Size when fully open.*—Small, averaging ¾ to 1 inch.

*Petalage.*—Double — averaging about 20 to 25 petals, arranged regularly with a few petaloids.

*Form.*—High centered circular form. Opens slowly, petals rarely reflexing below the sepals. Open flower reveals stamens.

Petals: Thick; well substanced; matt surface on inside and outside of petals.

*Shape.*—Outside petals, broad lanceolate with very short acute tip; intermediate — rounded lanceolate with short acute tip; inside petals arrow shaped with short acute tip; a few petaloids in the center.

Color: Newly opened flower from a plant grown at Chula Vista, Calif.:

*Outer petals, upper surface.*—Near azalea pink 618/3 page 74 tinged on outer portions with near jasper red o18 page 107.

*Outer petals, under surface.*—Near azalea pink 618/3 page 74, heavy brushing of near jasper red, o18 page 107.

*Intermediate petals, upper surface.*—Near azalea pink 618/3 page 74, tinged with near jasper red o18 page 107.

*Intermediate petals, under surface.*—Near azalea pink 618/3 page 74, tinged with near jasper red o18 page 107.

*Inner petals, upper surface.*—Near azalea pink 618/3 page 74.

*Inner petals, under surface.*—Near azalea pink 618/3 page 74.

Behavior: Opens well in all weather. Form excellent.

*Color.*—Long lasting.

*Flower longevity.*—Cut flowers at room temperature 5–7 days or longer. Outside in the sun 4–5 days or longer depending on temperature.

Reproductive organs:

*Stamens.*—Abundant, arranged regularly around pistils.

*Filaments.*—Varying lengths, short, yellow.

*Anthers.*—Well formed; yellow.

*Pollen.*—Small amount.

*Pistils.*—Small amount.

*Styles.*—Irregular, short, bunched, color greenish.

*Ovaries.*—All enclosed in calyx.

*Hips.*—Some.

*Sepals.*—Permanent; spear shaped; recurved.

*Seed.*—A few.

Foliage:

*Leaves.*—Compound of five (sometimes three, occasionally seven.) Fairly small; leathery; semi-glossy.

*Leaflets.*—Shaped: broad, nearly oval; apex acute; base rounded. Margin serrated.

*Color.*—Medium to dark green; new growth — darker with reddish tinge.

Rachis: Medium length; grooved; underside sparsely thorny otherwise smooth.

*Stipules.*—Medium length; narrow to medium width; narrow points with a slight recurving.

Growth:

*Habit.*—Dwarf; bushy; rounded; much branched.

*Growth.*—Vigorous for size.

*Canes.*—Medium; slender; sturdy.

*Main stems.*—Color: medium green.

*Thorns.*—Small; slender; hooked slightly downward; color: reddish. Prickles — none.

*Hairs.*—None.

*Branches.*—Color: medium green. Thorns: moderate number; medium length; slender; slightly curved upward.

The miniature rose plant and its flowers as herein described may vary in slight detail due to climatic, soil and cultural conditions under which the variety may be grown; the present description being of the variety as grown at Chula Vista, Calif.

I claim:

1. A new and distinct variety of miniature rose plant of hardy, dwarf, bushy, much branched habit, substantially as illustrated and described, characterized by buds and flowers similar in coloring to the variety, "Tiki," a floribunda, a near azalea pink 618/3 page 74, in the "R.H.S. Horticultural Colour Chart", and further characterized by a low growing, compact plant of micro-mini proportions.

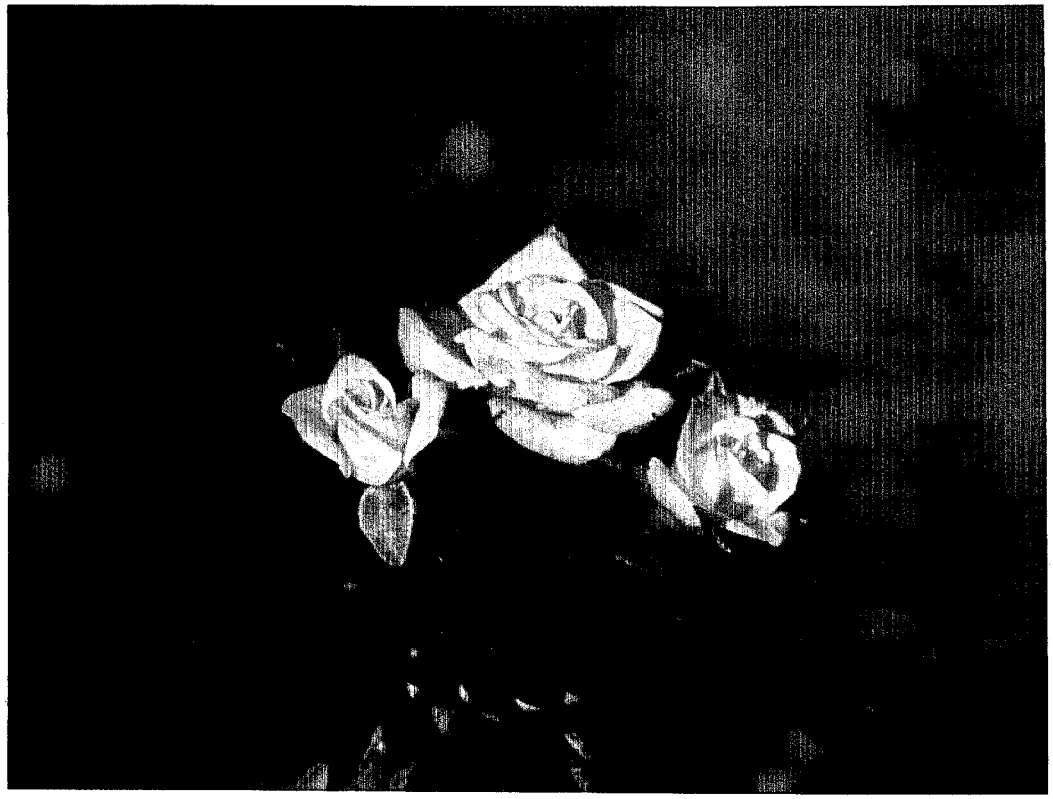

* * * * *